(12) United States Patent
Sawyer

(10) Patent No.: US 8,389,750 B2
(45) Date of Patent: Mar. 5, 2013

(54) PURIFICATION OF PROPYLENE OXIDE

(75) Inventor: Gary A. Sawyer, Media, PA (US)

(73) Assignee: Lyondell Chemical Technology, L.P., Houston, TX (US)

(*) Notice: Subject to any disclaimer, the term of this patent is extended or adjusted under 35 U.S.C. 154(b) by 343 days.

(21) Appl. No.: 12/924,457

(22) Filed: Sep. 28, 2010

(65) Prior Publication Data

US 2012/0077996 A1    Mar. 29, 2012

(51) Int. Cl.
  *C07D 301/19* (2006.01)
  *C07D 301/32* (2006.01)

(52) U.S. Cl. ........................ 549/529; 549/541

(58) Field of Classification Search ............. 549/529, 549/541
  See application file for complete search history.

(56) References Cited

U.S. PATENT DOCUMENTS

| | | |
|---|---|---|
| 2,550,847 A | 5/1951 | Mitchell et al. |
| 2,622,060 A | 12/1952 | Robeson et al. |
| 3,350,417 A | 10/1967 | Binning |
| 3,351,635 A | 11/1967 | Kollar |
| 3,464,897 A | 9/1969 | Jubin, Jr. |
| 3,477,919 A | 11/1969 | Lichtenwalter et al. |
| 3,578,568 A | 5/1971 | Washall |
| 3,843,488 A | 10/1974 | Schmidt et al. |
| 3,881,996 A | 5/1975 | Schmidt |
| 3,909,366 A | 9/1975 | Schmidt et al. |
| 4,140,588 A | 2/1979 | Schmidt |
| 4,367,342 A | 1/1983 | Wulff et al. |
| 4,691,034 A | 9/1987 | Sanderson et al. |
| 4,691,035 A | 9/1987 | Sanderson et al. |
| 4,692,535 A | 9/1987 | Larson et al. |
| 5,000,825 A | 3/1991 | Shih et al. |
| 5,006,206 A | 4/1991 | Shih et al. |
| 5,106,458 A | 4/1992 | Meyer et al. |
| 5,107,002 A | 4/1992 | Shih |
| 5,354,430 A | 10/1994 | Culbreth, III et al. |
| 6,500,311 B1 | 12/2002 | Sawyer |

OTHER PUBLICATIONS

PCT International Search Report and Written Opinion dated Jan. 26, 2012, corresponding to PCT Serial No. PCT/US/2011/053654.

*Primary Examiner* — Bernard Dentz

(57) ABSTRACT

The invention is a method of purifying propylene oxide containing acetone, water, methanol, methyl formate, aldehydes, and hydrocarbons impurities. The method comprises contacting the propylene oxide with a glycol and a $C_7$ or greater alkane in a liquid/liquid solvent extraction, and separating propylene oxide having reduced impurities content. The purified propylene oxide may be produced by reacting propylene and a hydroperoxide to produce a crude propylene oxide effluent, distilling the crude effluent to produce a propylene oxide stream which contains 1-5 weight percent of the impurities, contacting the propylene oxide stream with a glycol and a $C_7$ or greater alkane in a liquid/liquid solvent extraction, then separating an alkane fraction comprising propylene oxide from a glycol fraction, and distilling the alkane fraction in one or more steps to produce an alkane bottoms stream and a propylene oxide product having less than 0.1 weight percent impurities.

14 Claims, 1 Drawing Sheet

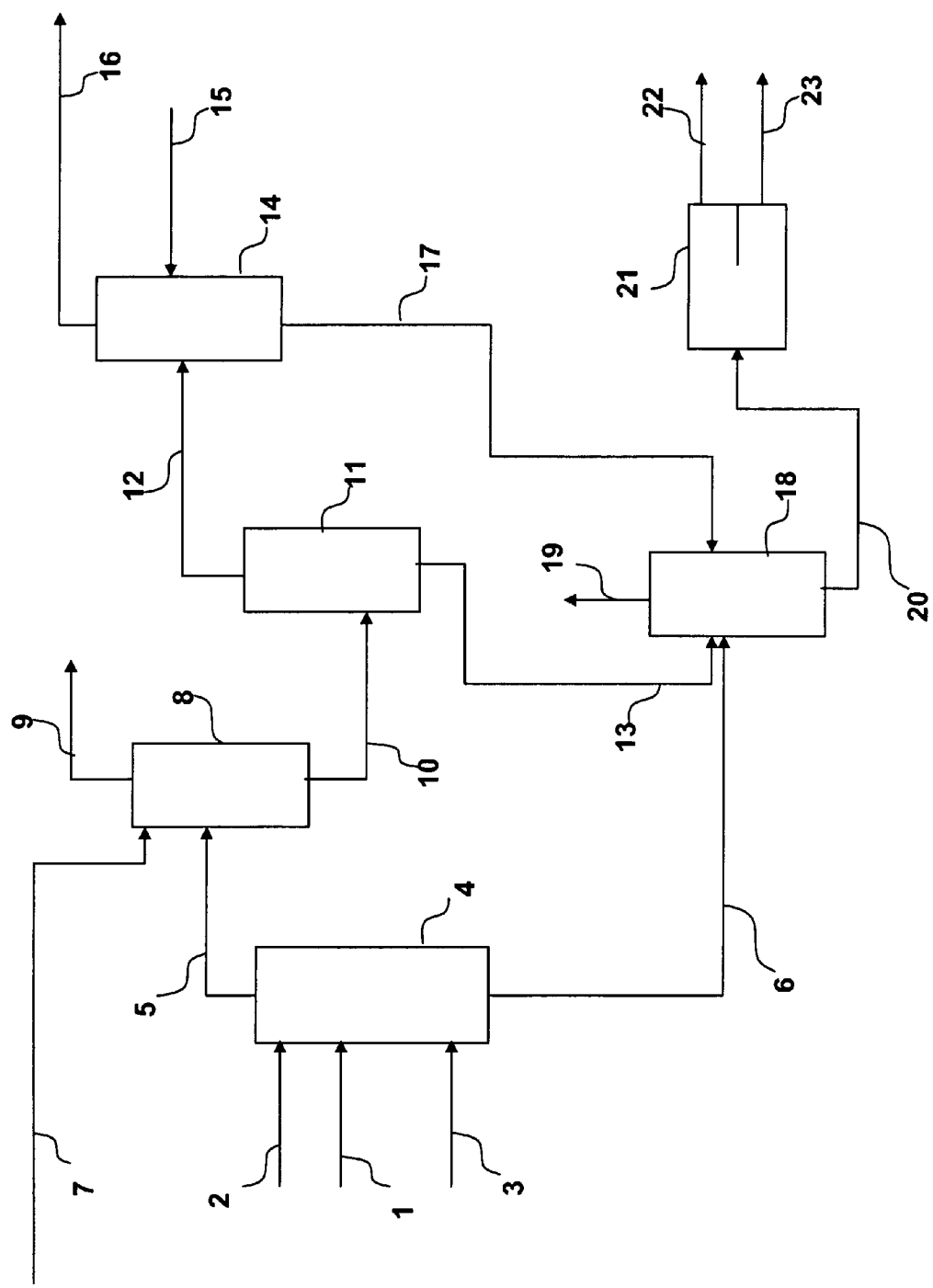

PURIFICATION OF PROPYLENE OXIDE

FIELD OF THE INVENTION

This invention relates to the purification of propylene oxide.

BACKGROUND OF THE INVENTION

Propylene oxide (PO) is a valuable chemical that is used to make propylene glycol, propylene glycol ethers, 1,4-butanediol, and polyols for use in the production of polyurethane materials. Generally, PO is formed by reacting propylene with an oxidizing agent in the presence of a catalyst. PO is commercially produced by reacting propylene with an organic hydroperoxide, such as ethyl benzene hydroperoxide, cumene hydroperoxide or tert-butyl hydroperoxide, in the presence of a solubilized molybdenum catalyst or a heterogeneous titania-on-silica catalyst. PO is also produced by the reaction of propylene and hydrogen peroxide in the presence of a titanium silicate catalyst.

In these processes, small amounts of water, hydrocarbons (typically $C_4$-$C_6$ alkanes and alkenes) and oxygen-containing byproducts, such as methanol, acetone, methyl formate, and aldehydes (acetaldehyde and propionaldehyde), are typically produced. Many methods have been developed to remove these impurities from PO. Previous disclosed methods include extractive distillation techniques which utilize: $C_8$ to $C_{20}$ alkanes, alkenes or naphthenes, $C_6$ to $C_{12}$ aromatic hydrocarbons, $C_8$ to $C_{12}$ aliphatic or cyclic paraffins, and a tertiary butyl alcohol-water mixture to remove contaminating hydrocarbons (see U.S. Pat. Nos. 3,843,488, 3,909,366, 3,464,897, 5,006,206); and water or lower glycols such as ethylene glycol and propylene glycol to remove oxygen-containing impurities (see U.S. Pat. Nos. 4,140,588, 3,578,568 and 5,000,825); and glycols and alkanes in sequential extractive distillation sections (see U.S. Pat. No. 5,354,430). Liquid-liquid extraction using water and a hydrocarbon such as n-octane as extractive solvents has also been taught to remove high quantities of methanol from a propylene oxide-methanol mixture (see U.S. Pat. No. 6,500,311).

Other purification processes include methods to remove methyl formate by contacting crude PO with metal hydroxides, including: an aqueous alkali metal hydroxide solution (see U.S. Pat. No. 2,622,060); an aqueous solution of an alkaline saponifying agent (see U.S. Pat. No. 2,550,847); an aqueous slurry of calcium hydroxide (see U.S. Pat. No. 3,477,919); and sodium hydroxide in water and glycerol (see U.S. Pat. No. 4,691,035). Other methods include using a combination of distillation and a caustic treatment to simultaneously aldolize acetaldehyde and saponify methyl formate (see U.S. Pat. No. 3,350,417) and treating with an aqueous calcium hydroxide slurry to which a solubilizer and an aldehyde scavenger are added (see U.S. Pat. No. 4,691,034).

Adsorption techniques have also been taught to remove high levels of impurities, including the removal of high molecular weight ethers from PO by treatment with an absorbent such as activated carbon (see U.S. Pat. No. 4,692,535) and the removal of methyl formate from contaminated PO by contacting with a basic ion exchange resin (see U.S. Pat. Nos. 5,107,002 and 5,106,458).

Commercially useful techniques include plural stage distillation processes to purify PO. See, for example, U.S. Pat. No. 3,881,996, which discloses distilling crude, propylene-free PO to remove acetaldehyde as an overhead product, then distilling the bottoms stream to separate PO as an overhead product from propionaldehyde and other higher boiling materials. This method can produce PO having very low levels of aldehyde (less than 10 ppm). However, distillation processes are extremely energy-intensive and there is a significant energy input required to achieve such low levels of aldehyde.

In sum, new methods for the purification of propylene oxide are needed. We have discovered an effective, convenient method to purify propylene oxide.

SUMMARY OF THE INVENTION

The invention is a method of purifying propylene oxide that contains impurities comprising acetone, water, methanol, methyl formate, aldehydes, and hydrocarbons. The method comprises contacting the impure propylene oxide with a glycol and a $C_7$ or greater alkane in a liquid/liquid solvent extraction, and separating propylene oxide having reduced impurities content. The purified propylene oxide may be produced by reacting propylene and a hydroperoxide to produce a crude propylene oxide effluent, distilling the crude effluent to produce a propylene oxide stream which contains 1-5 weight percent of the impurities, contacting the propylene oxide stream with the extractive solvent mixture, then separating an alkane fraction comprising propylene oxide from a glycol fraction, and distilling the alkane fraction in one or more steps to produce an alkane bottoms stream and a propylene oxide product having less than 0.1 weight percent impurities.

BRIEF DESCRIPTION OF THE DRAWING

FIG. 1 is a schematic flow diagram of one embodiment of the invention.

DETAILED DESCRIPTION OF THE INVENTION

Propylene oxide is a well-known chemical compound that is available from Lyondell Chemical Company and other producers. Propylene oxide may be produced by any known process, but is preferably the product of the reaction of propylene with a hydroperoxide such as an organic hydroperoxide or hydrogen peroxide. Preferably, the hydroperoxide is an organic hydroperoxide. Suitable organic hydroperoxides include ethyl benzene hydroperoxide, cumene hydroperoxide, and t-butyl hydroperoxide. Most preferably, the hydroperoxide is t-butyl hydroperoxide. The epoxidation process using organic hydroperoxides is described in U.S. Pat. Nos. 3,351,635 and 4,367,342. This epoxidation reaction preferably occurs in the presence of a solubilized molybdenum catalyst or a heterogeneous titania on silica catalyst. Following production of propylene oxide by epoxidation, the epoxidation reaction effluent is subjected to one or more distillation steps in order to produce a propylene oxide product stream.

Propylene oxide, as formed by the reaction of propylene with a hydroperoxide, contains various impurities. These impurities include acetone, water, methanol, methyl formate, aldehydes, and hydrocarbons. For example, a crude propylene oxide product produced by the reaction of propylene and an organic hydroperoxide such as t-butyl hydroperoxide, from which unreacted propylene has been removed by prior distillation according to conventional fractional distillation operations, typically contains 95-99 wt. % propylene oxide and 1 to 5 wt. % impurities, preferably from 2 to 4 wt. % impurities.

Following the reaction of propylene with a hydroperoxide such as t-butyl hydroperoxide, the propylene oxide product mixture is generally first distilled to separate unreacted propylene overhead from heavier components. The separated propylene is conveniently recycled to the epoxidation step.

The heavier components are then further purified in a series of purification steps to separate propylene oxide product and epoxidation co-product tert-butyl alcohol. The tert-butyl alcohol is preferably further purified before dehydration to isobutylene, which is a useful product in gasoline additives and synthetic polymers.

Purified propylene oxide, containing very low levels of impurities, can be produced from the epoxidation reaction effluent by subjecting the effluent to a series of distillation steps. However, the distillation steps have very high energy requirements that result in significant production cost. Thus, preferably the method of the invention comprises first reacting propylene and a hydroperoxide to produce a crude propylene oxide stream, and then distilling the crude propylene oxide stream to produce a propylene oxide stream containing 1 to 5 weight percent impurities comprising acetone, water, methanol, methyl formate, aldehydes and hydrocarbons. The propylene oxide stream is then contacted with a glycol and a $C_7$ or greater alkane in a liquid/liquid solvent extraction, and propylene oxide having reduced impurities content is then separated.

In order to reduce the level of impurities in the propylene oxide, the propylene oxide is subjected to a liquid-liquid solvent extraction step. The impure propylene oxide stream is contacted with a glycol and a $C_7$ or greater alkane. The glycol is immiscible with and has a higher density than the $C_7$ or greater alkane. Any glycol that is immiscible and has a different density than the $C_7$ or greater alkane may be used. Particular preferred glycols are selected from the group consisting of ethylene glycol, propylene glycol, glycerine, and mixtures thereof. The $C_7$ or greater alkane is preferably a $C_{8-9}$ alkane, and is more preferably octane, either branched or linear. The mixture of glycol and alkane preferably comprises about 20 to about 50 weight percent glycol and 50 to 80 weight percent alkane. The extractive solvent mixture:propylene oxide stream weight ratio is preferably from about 10:1 to about 2:1.

The glycol, $C_7$ or greater alkane, and the propylene oxide stream are preferably intimately mixed by any of a variety of different techniques. During the intimate mixing, a significant portion of the impurities passes into the glycol fraction, to an extent determined by the so-called partition coefficient of such substance in the conditions concerned. Liquid-liquid extraction processes may be operated batch-wise or continuously. The impure propylene oxide stream may be mixed with the glycol and $C_7$ or greater alkane in an agitated vessel, after which the layers of glycol and hydrocarbon are settled and separated. The extraction may be repeated if more than one contact is required. Most extraction equipment is continuous, with, e.g., successive stage contacts. Typical liquid extraction equipment includes mixer-settlers, vertical towers of various kinds which operate by gravity flow, agitated tower extractors, and centrifugal extractors.

The liquid-liquid extraction is conveniently carried out at moderate temperatures. Suitable temperatures are in the range of about 10° C. to 100° C., preferably 15° C. to 60° C. Pressures close to normal can suitably be employed. The liquid-liquid extraction is preferably performed in a tower that employs 1-20 theoretical stages, more preferably 5-15 stages.

The liquid-liquid extraction results in a hydrocarbon phase that comprises propylene oxide having a reduced impurities content and a glycol phase containing a significant portion of the impurities, particularly the more polar impurities such as methanol and water. These two phases are easily separated, and the propylene oxide-containing hydrocarbon phase may be further purified to produce high purity propylene oxide product. Conveniently, the $C_7$ or greater alkane in the hydrocarbon phase enhances the separation of some remaining impurities such as methyl formate from PO in extractive distillation schemes known in the art.

The glycol phase is preferably passed to a solvent stripper in order to remove the impurities that are in the glycol phase so that the glycol may be recycled to the liquid-liquid extraction step. The solvent stripper separates an overhead impurities stream comprising acetone, water, methanol, methyl formate, and aldehydes from a glycol bottoms stream that comprises purified glycol.

The hydrocarbon phase is preferably passed to a distillation column. The distillation column, the so-called "solvent lights column," separates an overhead lights stream comprising methanol, methyl formate, light aldehydes such as acetaldehyde, and light hydrocarbons such as isobutane from a hydrocarbon bottoms stream comprising propylene oxide and the $C_7$ or greater alkane solvent. The hydrocarbon bottoms stream will typically contain heavier aldehydes such as propionaldehyde, acetone, and heavier $C_6$ hydrocarbons. The solvent lights column is preferably an extractive distillation column that utilizes the $C_7$ or greater alkane solvent as an extractive distillation solvent. The column preferably operates at low pressure, more preferably at 0-20 psig (0–138 kPa) top pressure, with 20-60 theoretical stages. The solvent lights column overhead temperature is preferably maintained between about 20-55° C., and the bottoms temperature is preferably maintained between about 80-120° C.

The hydrocarbon bottoms stream is preferably taken into a second distillation column for the purification of propylene oxide. The so-called "propylene oxide purification column" separates a propylene oxide overhead stream from an alkane solvent bottoms stream that comprises propionaldehyde and acetone. The propylene oxide overhead stream may still contain a portion of the $C_6$ hydrocarbons. The propylene oxide purification column preferably operates at 0-10 psig (0–69 kPa) top pressure, with theoretical 40-70 stages. The propylene oxide purification column overhead temperature is preferably maintained between about 25-65° C., and the bottoms temperature is preferably maintained between about 140-180° C.

If necessary, the propylene oxide stream may be passed to another distillation column for removal of the remaining $C_6$ impurities (the "$C_6$ removal column"). The purified product propylene oxide is taken overhead and the $C_6$ hydrocarbons are removed as a $C_6$ bottoms stream. The purified propylene oxide typically contains less than 0.1 weight percent impurities, preferably less than 0.05 weight percent impurities. The $C_6$ removal column is preferably an extractive distillation column that a $C_{6-9}$ hydrocarbon solvent, most preferably the $C_7$ or greater alkane solvent, as an extractive distillation solvent. The $C_6$ removal column preferably operates at 0-10 psig (0–69 kPa) top pressure, with 20-50 theoretical stages. The $C_6$ removal column overhead temperature is preferably maintained between about 25-65° C., and the bottoms temperature is preferably maintained between about 140-180° C.

The alkane solvent bottoms stream from the propylene oxide purification column is preferably treated to purify the alkane solvent. The purified alkane solvent can preferably be recycled to the liquid-liquid extraction step or used as solvent in the solvent-lights column or $C_6$ removal column. Most preferably, the alkane solvent bottoms stream is passed to the solvent stripper along with the glycol phase from the liquid-liquid extraction. The overhead impurities stream is preferably removed and purged from the process. The solvent stripper preferably operates at atmospheric pressure and at a temperature between 55-135° C., with 10-25 stages.

The stripper bottoms stream, comprising glycol and alkane solvent, is preferably passed into a phase separator in order to separate the glycol from the alkane. The glycol is preferably recycled back to the liquid-liquid extraction step and the alkane may be recycled to the liquid-liquid extraction step, or used as the extractive distillation solvent in the solvent lights column or as the extractive distillation solvent in the $C_6$ removal column.

The following examples merely illustrate the invention. Those skilled in the art will recognize many variations that are within the spirit of the invention and scope of the claims.

EXAMPLE 1

Liquid-Liquid Extraction Using Glycol-Alkane Solvent Mixture

The epoxidation product stream is purified by a process as shown in FIG. 1. A crude propylene oxide product stream, produced by the reaction of propylene and tert-butyl hydroperoxide, containing by weight 96.9% PO, 1.9% acetone, 0.5% water, 0.3% methanol, 600 ppm methyl formate, 400 ppm propionaldehyde, 300 ppm acetaldehyde, and the remainder a mixture of hydrocarbons, is passed via line 1 fed into a liquid contacting device 4 that effects 11 theoretical stages of liquid extraction. The crude PO feed stream is fed into the liquid-liquid extractor at stage 4 from the top. Propylene glycol is fed via line 2 at the top of the contacting device 4. A mixture of branched $C_8$ and $C_9$ saturated hydrocarbons is fed via line 3 to the bottom of the device 4. The ratio by weight of PO:glycol:hydrocarbon streams is 1:1:2. PO is recovered in the light hydrocarbon phase via line 5 with 99.7% efficiency, while 99.99% of water and 99.4% of methanol is rejected in the heavy glycol phase via line 6. In addition, 64% of the acetaldehyde, 32% of the propionaldehyde, 12% of the acetone, and 1% of the methyl formate is rejected in the heavy glycol phase stream via line 6. Essentially all of the hydrocarbon impurities in the crude PO remain in the light phase stream. The liquid-liquid extraction using a glycol and a $C_7$ or greater alkane effectively removes a significant amount of the impurities from the propylene oxide.

In a further preferred embodiment of the invention, the light hydrocarbon phase is passed via line 5 to a solvent lights distillation column 8, which is also fed via line 7 with a $C_{7-10}$ hydrocarbon as an extractive distillation solvent. The ratio of solvent (in line 7) to crude PO (in line 1) is 3.9:1. Column 8 has 43 theoretical stages with feed line 5 at stage 15 from the top and solvent line 7 at stage 5 from the top. The column is operated at 10 psig (69 kPa) with temperatures from 38° C. to 81° C., a distillate:crude PO feed ratio of 0.0058, and a reflux:crude PO feed ratio of 1.1. An overhead lights stream comprising all the remaining methanol, methyl formate, light aldehydes such as acetaldehyde, and light hydrocarbons such as isobutane is removed via line 9. A hydrocarbon bottoms stream comprising propylene oxide and alkane solvent (plus propionaldehyde, acetone, and heavier $C_6$ hydrocarbons) is removed via line 10 and passed to a propylene oxide purification column 11. Column 11 has 68 theoretical stages with feed line 10 at stage 39 from the top. The column is operated at 10 psig (69 kPa) with temperatures from 50° C. to 141° C., and a reflux ratio of 2.3. A propylene oxide overhead vapor stream (containing a minor amount of the $C_6$ hydrocarbons) is removed via line 12 and an alkane solvent bottoms stream that contains propionaldehyde and acetone is removed via line 13.

The propylene oxide overhead stream is preferably passed via line 12 to a $C_6$ removal column 14, which is also fed with a $C_{6-10}$ hydrocarbon as an extractive distillation solvent via line 15. Column 14 has 43 theoretical stages with feed line 12 on stage 39 from the top and solvent line 15 on stage 16 from the top. The column is operated at 7 psig (48 kPa) with temperatures from 46° C. to 142° C., and a reflux ratio of 0.6. Purified product propylene oxide is taken overhead via line 16 and the $C_6$ hydrocarbons are removed as a $C_6$ bottoms stream via line 17.

Preferably, a solvent stripper 18 is fed with the heavy glycol phase via line 6, the alkane solvent bottoms stream via line 13, and the $C_6$ bottoms stream via line 17. Solvent stripper 18 has 18 theoretical stages with all feeds fed on stage 6 from the top. The column is operated at 3 psig (21 kPa) with temperatures from 58° C. to 127° C., a distillate:crude PO ratio of 0.06 and a reflux:crude PO ratio of 1.1. The impurities are removed as an overhead via line 19 and the bottoms alkane-glycol mixture is removed via line 20 and passed to a phase separator 21 in order to separate the glycol from the alkane. The glycol is removed via line 23 and may be preferably recycled back to the liquid-liquid extracter by adding to line 2. The alkane is removed via line 22 and may be recycled to the liquid-liquid extracter by adding to line 3, or may be used as the extractive distillation solvent in the solvent lights column 8 by adding to line 7 or as the extractive distillation solvent in the $C_6$ removal column 14 by adding to line 15.

COMPARATIVE EXAMPLE 2

Liquid-Liquid Extraction Using Water-Alkane Solvent Mixture

Comparative Example 2 is run according to the procedure of Example 1 with the exception that water is used in place of glycol in line 2 such that the ratio by weight of PO:water:alkane is 1:1:2. By comparison, only 45% of the acetaldehyde and 0.5% of the propionaldehyde is removed into the polar water phase.

In addition, the use of water impacts downstream processing as well, as some is dissolved in the extraction line 5. Water is a lighter boiler than glycols; in fact, water is lighter than the preferred hydrocarbon solvent whereas glycols are heavier. This makes water removal from product PO line 16 more difficult than glycol removal from PO.

I claim:

1. A method of purifying propylene oxide containing acetone, water, methanol, methyl formate, aldehydes, and hydrocarbon impurities, said method comprising contacting the propylene oxide with a glycol and a $C_7$ or greater alkane in a liquid/liquid solvent extraction, and separating an alkane fraction comprising propylene oxide having reduced impurities content.

2. The method of claim 1 wherein the glycol is selected from the group consisting of ethylene glycol, propylene glycol, glycerine, and mixtures thereof.

3. The method of claim 1 wherein the $C_7$ or greater alkane is a $C_{8-9}$ alkane.

4. The method of claim 1 further comprising distilling the alkane fraction in one or more steps to produce a purified propylene oxide product.

5. The method of claim 1 wherein the propylene oxide is produced by the reaction of propylene and an organic hydroperoxide.

6. The method of claim 5 wherein the organic hydroperoxide is t-butyl hydroperoxide.

7. The method of claim 1 wherein the propylene oxide contains from 1 to 5 weight percent impurities.

8. A method which comprises: (a) reacting propylene and a hydroperoxide to produce a crude propylene oxide effluent;

(b) distilling the crude propylene oxide effluent to produce a propylene oxide stream containing 1 to 5 weight percent impurities comprising acetone, water, methanol, aldehydes and hydrocarbons; (c) contacting the propylene oxide stream with a glycol and a $C_7$ or greater alkane in a liquid/liquid solvent extraction; (d) separating an alkane fraction comprising propylene oxide having reduced impurities content from a glycol fraction; (e) distilling the alkane fraction in one or more steps to produce an alkane bottoms stream and a propylene oxide product having less than 0.1 weight percent impurities.

9. The method of claim 8 wherein the glycol is selected from the group consisting of ethylene glycol, propylene glycol, glycerine, and mixtures thereof.

10. The method of claim 8 wherein the $C_7$ or greater alkane is a $C_{8-9}$ alkane.

11. The method of claim 8 wherein the hydroperoxide is t-butyl hydroperoxide.

12. The method of claim 8 further comprising passing the glycol fraction and the alkane bottoms stream to a solvent stripper, removing impurities as a stripper overhead stream and an alkane and glycol mixture as an alkane-glycol bottoms stream, and passing the alkane-glycol bottoms stream to a phase separator to separate a glycol recycle stream from an alkane recycle stream.

13. The method of claim 12 wherein the glycol recycle stream is recycled to the liquid/liquid solvent extraction of step (c).

14. The method of claim 12 wherein the alkane recycle stream is recycled to the liquid/liquid solvent extraction of step (c) or is used as an extractive distillation solvent in any of the one or more distillations of step (e).

* * * * *